United States Patent
Sultan et al.

(10) Patent No.: US 10,130,662 B2
(45) Date of Patent: Nov. 20, 2018

(54) THERAPEUTIC AGENT DELIVERY SYSTEM AND METHOD FOR ARTERIES

(71) Applicant: TULIP ENDOVASCULAR INNOVATION LIMITED, Galway (IE)

(72) Inventors: Sherif Sultan, Galway (IE); Niamh Hynes, Galway (IE)

(73) Assignee: Tulip Endovascular Innovation Limited, Galway (IE)

( * ) Notice: Subject to any disclaimer, the term of this patent is extended or adjusted under 35 U.S.C. 154(b) by 235 days.

(21) Appl. No.: 15/028,822

(22) PCT Filed: Oct. 20, 2014

(86) PCT No.: PCT/EP2014/072450
§ 371 (c)(1),
(2) Date: Apr. 12, 2016

(87) PCT Pub. No.: WO2015/059099
PCT Pub. Date: Apr. 30, 2015

(65) Prior Publication Data
US 2016/0256501 A1 Sep. 8, 2016

(30) Foreign Application Priority Data
Oct. 22, 2013 (EP) .................................. 13189732

(51) Int. Cl.
*A61K 35/545* (2015.01)
*A61M 25/10* (2013.01)
(Continued)

(52) U.S. Cl.
CPC .......... *A61K 35/545* (2013.01); *A61K 9/0014* (2013.01); *A61K 35/19* (2013.01);
(Continued)

(58) Field of Classification Search
CPC .... A61K 35/545; A61K 9/0014; A61K 35/19; A61K 38/36; A61K 38/39; A61K 38/18;
(Continued)

(56) References Cited

U.S. PATENT DOCUMENTS

2002/0188253 A1* 12/2002 Gordon ............ A61B 17/12045
604/101.03
2009/0131950 A1 5/2009 Liu et al.

OTHER PUBLICATIONS

International Search Report issued in PCT/EP2014/072450; dated Mar. 6, 2015.
(Continued)

*Primary Examiner* — Amber Stiles
(74) *Attorney, Agent, or Firm* — Studebaker & Brackett PC (57) ABSTRACT

A delivery system for delivery of a therapeutic agent such as stem cells into a vein and across a micro circulation system into an artery comprises a multi lumen catheter for delivery of a therapeutic agent. A discharge device is located in a vein. The operation of the delivery device is controlled by a pressure stem cell solution delivery gun system. There are multiple delivery stages. These may include delivery of an elixir to open up the pressure bed, a platelet-rich plasma, stem cells, scaffolds, and finally an elixir to provide emichment and nourishment of the stem cells.

12 Claims, 7 Drawing Sheets

(51) Int. Cl.
*A61K 9/00* (2006.01)
*A61K 35/19* (2015.01)
*A61K 38/18* (2006.01)
*A61K 38/36* (2006.01)
*A61K 38/39* (2006.01)
*A61M 5/20* (2006.01)
*A61M 25/00* (2006.01)

(52) U.S. Cl.
CPC .............. *A61K 38/18* (2013.01); *A61K 38/36* (2013.01); *A61K 38/39* (2013.01); *A61M 5/20* (2013.01); *A61M 25/0026* (2013.01); *A61M 25/1011* (2013.01)

(58) Field of Classification Search
CPC . A61M 25/0026; A61M 5/20; A61M 25/1011
See application file for complete search history.

(56) References Cited

OTHER PUBLICATIONS

Written Opinion issued in PCT/EP2014/072450; dated Mar. 6, 2015.
Sultan, Sherif et al.; "Critical appraisal of stem cell therapy in peripheral arterial disease: Do current scientific breakthroughs offer true promise or false hope?"; J. Biomedical Science and Engineering; 2014; pp. 75-85.
Sultan, Sherif et al; "Stem Cell Smart Technology, where are we now and how far we have to go?"; Vascular; 2017; pp. 1-13.
International Preliminary Report on Patentability and Written Opinion of the International Searching Authority; PCT/EP2014/072450 dated Apr. 26, 2016.

\* cited by examiner

THERAPEUTIC AGENT DELIVERY SYSTEM AND METHOD FOR ARTERIES

INTRODUCTION

This invention relates to a delivery system for a therapeutic agent, particularly stem cells and to methods for delivery of therapeutic agents such as stem cells, especially for the treatment of vascular occlusions.

Stem cells are biological cells found in all multicellular organisms that can divide and differentiate into varied specialised cell types. They can self-renew to produce more stem cells. In mammals, there are two broad types of stem cells: embryonic stem cells, which are isolated from the inner cell mass of blastocysts, and adult stem cells, which are found in various tissues. In adult organisms, stem cells and progenitor cells act as a repair system for the body, replenishing debilitated adult tissues. In a developing embryo, stem cells can differentiate into specialised cells called pluripotent cells. They maintain the normal turnover of regenerative organs, such as blood, skin, or intestinal tissues. Adult stem cells can also be programmed to differentiate into Induced pluripotent stem cells.

Angiogenesis is essential for vascular tissue engineering and is the process by which the pre-existing vasculature gives form to new blood vessels. The process is based on various angiogenic factors to form functional blood vessels. Several growth factors have been applied to therapeutic angiogenesis, including the angiopoietins, hepatocyte growth factor (HGF), FGF (acidic and basic), and VEGF. Among these stimulators, VEGF is one of the major groups of proteins involved in blood vessel formation, by directly stimulating endothelial cells migration and proliferation; the VEGFs include VEGF-A, -B, -C, -D, -E and -F.

After VEGF, the FGFs are the most widely applied proteins for restoration of the blood supply in ischemic tissues, and these stimulate re-endothelialization of wounded arteries; in particular, bFGF binds to endothelial cells and enhances their migration and proliferation for new blood vessel formation. HGF, neurotrophin, erythropoietin, and IGF are all also used for targeted vascular repair. In addition to other growth factors, such as Platelet Derived Growth Factor (PDGF), epherin B2, and angiopoietin 1, these help to stabilize the newly shaped blood vessels, by recruiting smooth muscle cells to the nascent endothelial capillary. Angiopoietins 1 and 2 function through the Tie2 receptor, which controls signal survival, migration of endothelial cells, regulation of blood vessel remodeling, and maintenance of vascular integrity.

Fibrinogen (Fbg) and Fibrin (Fbn) are blood proteins which have the ability to augment the biochemical and mechanical integrity of the scaffold for vascular regeneration. The enzymatic fragmentation of fibrin yields a variety of degradation products that are capable of inducing angiogenesis; in particular, Fbn fragment E is a potent angiogenic factor. Heparin-functionalized Fbn matrix immobilized with VEGF has been shown to be highly effective in delivering the growth factor over a period of months. Similarly, bFGF-incorporated Fbn scaffolds have shown a comparatively slow release, for continuous angiogenesis. Fbn scaffolds derived from blood clots can be used as a local injectable carrier for VEGF, as this approach prevents the initial burst-release issue and maintains a controlled release. Both VEGF- and bFGF-immobilized Fbn-based scaffold systems have shown increased neovascularization, with the establishment of more mature blood vessels compared with the delivery of single growth factors. Both Fbg and Fbn contain binding sites for various angiogenic factors, including adipose-derived stem cells and bone marrow stem cells. Both Fbg and Fbn provide a high seeding efficacy with uniform cell distribution for certain stem cells, such as hematopoietic stem cells, endothelial progenitor cells, smooth muscle cells, and MSCs. Smooth muscle cells can easily bind with Fbn via integrin, evoking a number of biochemical responses, such as secretion of proteolytic enzymes and production of the extracellular matrix collagen and elastin, which lead to Fbn degradation and increased mechanical strength, respectively, aiding in the formation of blood vessels.

Platelet Rich Plasma (PRP) enables healing through the use of one's own natural growth factors. Platelets contain an abundance of growth factors and cytokines that can affect inflammation, postoperative blood loss, infection, wound and soft tissue healing. Platelets also release many bioactive proteins responsible for attracting macrophages and mesenchymal stem cells that not only promote removal of degenerated and necrotic tissue, but also enhance tissue regeneration and healing.

The invention is directed towards optimizing delivery of therapeutic agents to a blood vessel.

STATEMENTS OF INVENTION

According to the invention, there is provided a delivery system for delivery of a therapeutic agent into a vein and across a micro circulation system into an artery. In one embodiment, the therapeutic agent comprises stem cells. In one embodiment, the therapeutic agent comprises proteins, multiple growth factors, fibrinogen and fibrin nano-scaffolds, platelet rich plasma and/or pharmaceutical agents.

In one embodiment, the system comprises a multi-lumen catheter. In one embodiment, the system comprises a discharge device for location in a vein. In one embodiment, the discharge device is mounted to the catheter. In one embodiment, at least one lumen of the catheter is used to control the operation of the stem cell discharge device.

In one embodiment, the system comprises a first balloon which is located proximally of the delivery device. In one embodiment, the system comprises a second balloon which is located distally of the delivery device. In one embodiment, the operation of the delivery device is controlled by a pressure stem cell solution delivery system, which may be operated by a gun. In one embodiment, the stem cell delivery system is supplied by a canister, and there may be a plurality of canisters.

In one embodiment, the system is adapted to deliver the therapeutic agent by infusion. In one embodiment, the system is adapted to deliver the therapeutic agent under a pressure of up to 90 mmHg.

In one embodiment, the system is adapted to deliver the therapeutic agent at a flow rate in the range of 0.3 to 1.4 ml/min. In one embodiment, the system is adapted to deliver the therapeutic agent for a duration of up to 120 mins.

In one embodiment, the system is adapted to deliver different therapeutic agents in successive stages, each with a corresponding set of delivery parameters. In one embodiment, the agents include an elixir stem cell solution to open collapsed venules for infusion across a micro-circulation system. In one embodiment, the elixir delivery is at a pressure up to 90 mmHg. In one embodiment, the elixir delivery is for a duration in the range of 10 min to 20 min.

In one embodiment, the agents include platelet-rich plasma delivered after the elixir to prepare the vascular bed for delivery of stem cells. In one embodiment, the platelet-rich plasma is delivered at a pressure of up to 90 mmHg. In one embodiment, the plasma delivery is for a duration in the range of 10 min to 20 min.

In one embodiment, the system is adapted to deliver stem cells and growth factors in a third stage after said plasma delivery. In one embodiment, the delivery pressure is under 25 mmHg. In one embodiment, the flow rate for this stage is in the range of 0.33 to 0.44 ml/min.

In one embodiment, the system is adapted to deliver scaffolds in a fourth stage after said third stage. In one embodiment, the delivery pressure for this stage is under 25 mmHg. In one embodiment, the flow rate is in the range of 0.33 to 0.44 ml/min.

In one embodiment, the system is adapted to deliver an elixir in a fifth stage after said scaffold delivery. In one embodiment, the delivery pressure is under 25 mmHg. In one embodiment, the flow rate is in the range of 0.33 to 0.44 ml/min In another aspect, the invention provides a method for treatment of an occlusion in an artery comprising the step of delivering a therapeutic agent into a venous system, across a microcirculation system and into the artery, or into a microcirculation system and onwards to the artery. In one embodiment, the therapeutic agent includes stem cells.

In one embodiment, the method comprises maintaining a thermo-balanced environment at a temperature of from 34° C. to 37° C. In one embodiment, the therapeutic agent is delivered under a pressure from neutral pressure to 90 mm Hg.

In one embodiment, the delivery is at a pressure which is dependent on a pressure wire sensor gradient at the desired location of delivery. In one embodiment, a plurality of agents are delivered from a plurality of reservoirs. In one embodiment, each reservoir comprises a canister which may contain about 40 ml, and there may be five such canisters.

In one embodiment, a first reservoir contains elixir stem cells solution which is delivered to a desired location in order to open collapsed venules. In one embodiment, the elixir delivery is for a duration in the range of 10 min to 20 min.

In one embodiment, a second reservoir contains autologous platelet rich plasma which is delivered to a desired location in a micro circulation system to prepare the vascular bed for the delivery of stem cells. In one embodiment, the platelet-rich plasma is delivered at a pressure of up to 90 mmHg. In one embodiment, the plasma delivery is for a duration in the range of 10 min to 20 min.

In one embodiment, a third reservoir contains allogenic stem cells and growth factors. In one embodiment, said delivery is at a pressure not exceeding 25 mmHg. In one embodiment, the agent includes stem cells, and wherein said delivery of allogenic stem cells and growth factors is at a flow rate of 0.33-0.44 ml/min over a period of 45-60 min, so as not to damage the stem cells and their functional capacity.

In one embodiment, a fourth reservoir contains scaffolds which are delivered to a desired location to promote sustained release of growth factors. In one embodiment, said scaffolds are Fibrin and Fibrinogen nano-scaffolds. In one embodiment, the delivery pressure of the scaffolds is under 25 mmHg. In one embodiment, the flow rate is in the range of 0.33 to 0.44 ml/min In one embodiment, a fifth reservoir contains elixir stem cells solution which is delivered to a desired location in order to sustain the viability of the previously delivered agents. In one embodiment, the delivery pressure is under 25 mmHg. In one embodiment, the flow rate is in the range of 0.33 to 0.44 ml/min.

According to the invention there is provided a delivery system for delivery of a therapeutic agent into a vein and across a micro circulation system into an artery. In one case the therapeutic agent comprises stem cells.

The therapeutic agent may comprise proteins, multiple growth factors, fibrinogen and fibrin nano scaffolds, platelet rich plasma and/or pharmaceutical agents.

In one embodiment the delivery system comprises a multi lumen catheter for delivery of a therapeutic agent. The delivery system may comprise a discharge device for location in a vein.

In one case the discharge device is mounted to the catheter.

In one aspect at least one lumen of the catheter is used to control the operation of the stem cell discharge device.

In one embodiment the system comprises a first balloon which may have a proximal radio-opaque marker and is located proximally of the delivery device. The system may comprise a second balloon which may have a distal radio-opaque marker which is located distally of the delivery device.

In one case the operation of the delivery device is controlled by a hydraulic system.

In another embodiment the operation of the delivery device is controlled by a pressure stem cell solution delivery gun system. In one case the stem cell delivery gun system is supplied by a canister. There may be a plurality of canisters.

Also provided is a method for treatment of an occlusion in an artery comprising the step of delivering a therapeutic agent into a venous system, across a microcirculation system and into an artery.

Further provided is a method for delivery of stem cells to a desired location comprising delivering stem cells into the venous system.

Also provided is a method for delivery of stem cells to a desired location comprising delivering stem cells into a micro circulation system.

The invention also provides a method for delivery of stem cells to a desired location in an artery comprising delivering stem cells into a venous system and across a micro circulation system into an artery.

The invention provides a method for delivery of stem cells to a desired location comprising delivering stem cells into a micro circulation system in a thermo-balanced environment at a temperature of from 34 to 37 degrees C.

Also provided is a method for delivery of stem cells to a desired location comprising delivering stem cells into a micro circulation system under a pressure from neutral pressure up to 120 mmHg.

Further provided is a method for delivery of stem cells to a desired location comprising delivering stem cells into a micro circulation system in which delivery is at a pressure which is dependent on a pressure wire sensor gradient at the desired location of delivery.

In one embodiment the invention provides a method for delivery of stem cells to a desired location comprising delivering fluid from a plurality of reservoirs into a micro circulation system. Each reservoir may comprise a canister which may contain about 40 ml. There may be 5 such canisters.

A first canister may contain elixir stem cells solution which is delivered to a desired location in a micro circulation system in order to open collapsed venules.

A second canister may contain autologous platelet rich plasma which is delivered to a desired location in a micro circulation system to prepare the vascular bed for the delivery of stem cells.

A third canister may contain allogenic stem cells and growth factors which are delivered to a desired location in a micro circulation system.

A fourth canister may contain Fibrin and Fibrinogen nanoscaffolds which are delivered to a desired location in a micro circulation system to promote sustained release of growth factors.

A fifth canister may contain elixir stem cells solution which is delivered to a desired location in a micro circulation system in order to sustain the viability of the previously delivered solutions.

According to the invention there is provided a method of delivering stem cells to the vascular circulation system wherein the delivery of stem cells is through the venous system to the venous side of the microcirculation system thereby deploying cells to the venules. The stem cells may be used to treat vascular conditions. The delivery of stem cells is achieved using a multi lumen catheter. Also provided is a method of delivering stem cells to the micro circulation system. Further provided is a method of delivering stem cells to the arterial system from the venous system. Also provided is a method of promoting angiogenesis. The invention also provides a method of treating occluded (blocked) or stenosed (narrowed) arteries through the venous system and a method of treating occluded or stenosed arteries through the venous system with stem cells by delivering stem cells through the venous system.

One important advantage of the invention is that it is not necessary to disturb an occlusion in atheromatous plaque in order to deliver a therapeutic agent. The therapeutic agent can access the distal side of an occlusion or stenosis. The risk of embolic material being released from an atheromatous plaque during a procedure is avoided. Such released embolic material could have catastrophic consequences for a patient.

BRIEF DESCRIPTION OF THE DRAWINGS

The invention will be more clearly understood from the following description of some embodiments thereof, given by way of example only, with reference to the accompanying drawings, in which.

DETAILED DESCRIPTION

We describe locations for stem cell delivery to yield optimum restoration of vascular function in a vessel such as an artery, a method of delivery that is new in its approach, and a device to effect the deployment of the stem cell to the specific desired location.

The device and method in one embodiment provide delivery of stem cells for the treatment of Vascular Occlusive Disease and Peripheral Vascular Disease. In the lower limbs this includes such conditions as Critical Lower Limb Ischemia caused by arterial blockage. We describe a location for delivery of stem cells, proteins, multiple growth factors, fibrinogen and fibrin nano scaffolds, platelet rich plasma and pharmaceutical agents to yield optimum restoration of vascular function in that region, a method of delivery that is new in its approach, and a device to effect the deployment of the stem cells to the specific desired location.

In the invention a therapeutic agent, particularly stem cells may be delivered to the microcirculation system anywhere in the body. There are microcirculation systems of arterial to venous blood transitions located all over the body. The method of the present invention could be applied to any of those. The methodology presented here is described by way of example as it applies to treating vascular conditions in the lower limbs, however it could equally apply to anywhere else in the body where there are micro-circulation systems between veins and arteries. In the invention the venous system is used to treat peripheral arterial occlusive diseases opposed to delivery directly into the arterial system. Using the methodology of this invention stem cell, proteins, multiple growth factors, fibrinogen and fibrin nano scaffolds, platelet rich plasma and pharmaceutical agents are delivered to the microcirculation system, which is accessed endovascularly through the common femoral vein as a conduit to the deep venous system. A catheter is inserted into the femoral vein using a percutaneous approach at the groin, just above the sapheno femoral junction. A multi-lumen catheter is used as the means of transporting and deploying the stem cells, proteins, multiple growth factors, fibrinogen and fibrin nanoscaffolds, platelet rich plasma and pharmaceutical agents to the microcirculation system.

This invention may be used to treat all vascular occlusion related conditions. Such conditions include: critical lower limb ischemia, upper limb critical ischemia, venous ulcers, diabetic foot ulcers, claudication, rest pain, gangrene, Raynaud's disease, thromboangiitis obliterans, and vasculitis.

Prior to treatment with the present device patients are required to be off statins, Non-Steroidal Anti-Inflammatory Drugs, Drug-modified Rheumatoid Arthritis Drugs, Antibiotics, and Vitamin K antagonists for at least 90 days. Patients are treated with Filgrastim (Granulocyte-colony stimulating factor, G-CSF) administered subcutaneously in the arm at 10 mcg/kg every 3 days of a total of 10 days prior to treatment with the device. Heparin and Lidocaine are contraindicated during stem cell treatment due to their toxic effect on stem cells.

In the invention, stem cells, proteins, multiple growth factors, fibrinogen and fibrin nano scaffolds, platelet rich plasma and pharmaceutical agents are delivered to the arteriole through the venules, metarterioles, and capillaries in the microcirculation system. The therapeutic agents travel across through the microcirculation system after being discharged. There is a variation in pressure to be overcome which varies by increasing across this pathway from about 10 mm/Hg at the venules side to over 120 mm/Hg at the arteriole. However the pressure in the arteriole will be considerably reduced or even absent in cases where there is a blockage (occlusion) or narrowing (stenosis) in the artery proximal to arteriole. The discharge of the therapeutic agents has sufficient energy to overcome this pressure differential.

Alternatively, a simpler system of injecting the suspension directly into the catheter at the proximal end may prove effective. However, it is envisaged that this would at least consume substantially more of the valuable stem cell suspension.

In one embodiment of the device the therapeutic agents will be delivered from the proximal end of the catheter under variable pressure from a stem cell delivery gun. Multiple therapeutic solutions can be delivered at the same treatment setting by filling separate canisters with each agent. The canisters will be loaded in the gun handle and deployed under pressures through the catheter lumen to the delivery zone on the lower end of the catheter. Flushing solution can be loaded in a canister at various stages of the procedure to ensure that the therapeutic agents are flushed out of the catheter lumen and into the treatment zone.

In the invention the venous system is used to treat blockage problems in the arterial system. The root cause of the problems that require treatment is that the artery is blocked (also referred to as occluded or stenosed). In the example illustrated in FIG. 2 the anterior tibial artery is occluded. A common approach to addressing this problem currently is to insert a catheter directly into the artery to remove the occlusion. The methods of blockage removal can be mechanical cutting and erosion of the plaque or the application of cold excimer laser pulses to break down the plaque is also effective. These approaches are more suitable to short and small blockages. They carry the risk of damage to the artery and of further embolization occurring elsewhere in the body. The length of the occlusion can extend over the length of the artery to 20 cm.

In one embodiment of the invention a stem cell discharge device is located in the deep vein adjacent to the branch which accesses and branches into venules to treat the arterial occlusion by repair of the occluded artery and/or any formation of new arteries (angiogenesis). This invention will overcome the side effects of adding local anaesthetics to intra muscular leg injections as this destroys the stem cell instantaneously.

This stem cell discharge device of the invention may be mounted at the distal end of a multi-lumen catheter. Proximal to the stem cell discharge device on the catheter is a small or short balloon. For use in the anterior tibial vena comitantes the balloon may be typically 3.5 mm in diameter. The purpose of the balloon is to occlude the vein and prevent the stem cells from travelling back proximally through the vein. There is a second balloon at the distal end of the stem cell discharge device to occlude the vein and prevent stem cells travelling forward. The distal balloon may be 2.5 mm in diameter. The balloons may be pressurized to any suitable pressure such as about 14 atmospheres (Bar).

The stem cells are suspended in a liquid suspension to maintain their viability.

Figure 1:
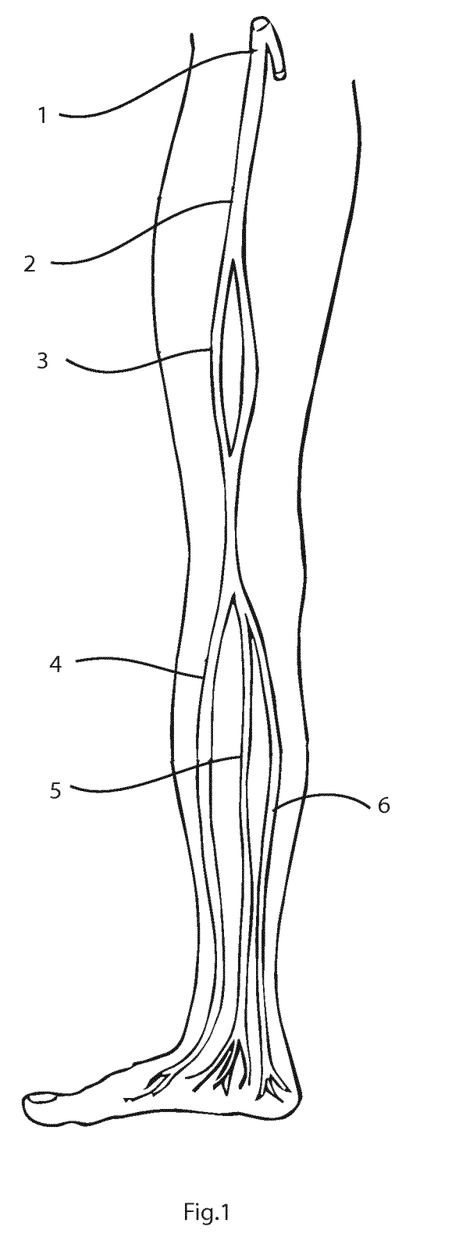
FIG. 1 is a diagram of part of the vascular anatomy illustrating points of access and points of delivery.

Referring to FIG. 1 the treatment area in one example includes the common femoral vein 1, the superficial vein 2, the popliteal vein 3, the anterior tibial vena comitanta 4, the posterior tibial vena comitanta 5, and the peroneal vein 6.

Figure 2:
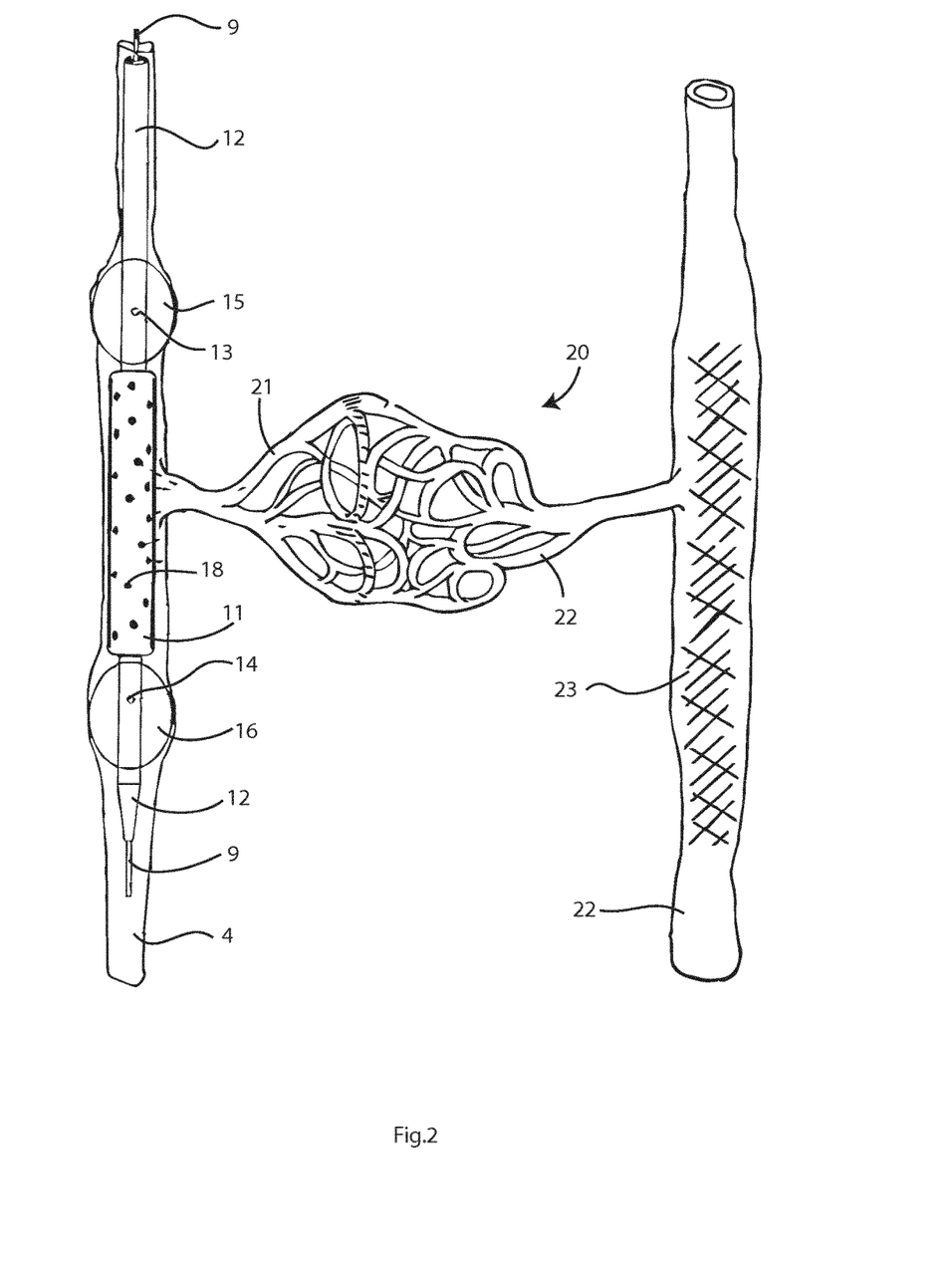
FIG. 2 is a diagram illustrating stem cell delivery to the microcirculation system using a delivery method and system of the invention.

Referring to FIG. 2 a delivery device of the invention includes a guide wire 9 (0.014 for anterior tibial vena comitantes with pressure sensor). Item 12 is a multi-lumen catheter. There is a proximal occlusion balloon 15 and a distal occlusion balloon 16, and these have inflation ports 13 and 14 respectively. The discharge device 11 is between these balloons.

The device may be located in a vein at the junction with a micro circulation system 20 having venules, metarterioles, and capillaries 21 and an arteriole 22. The micro circulation system 21 links the vein 4 with an artery, the anterior tibial artery which is blocked.

Figure 3:
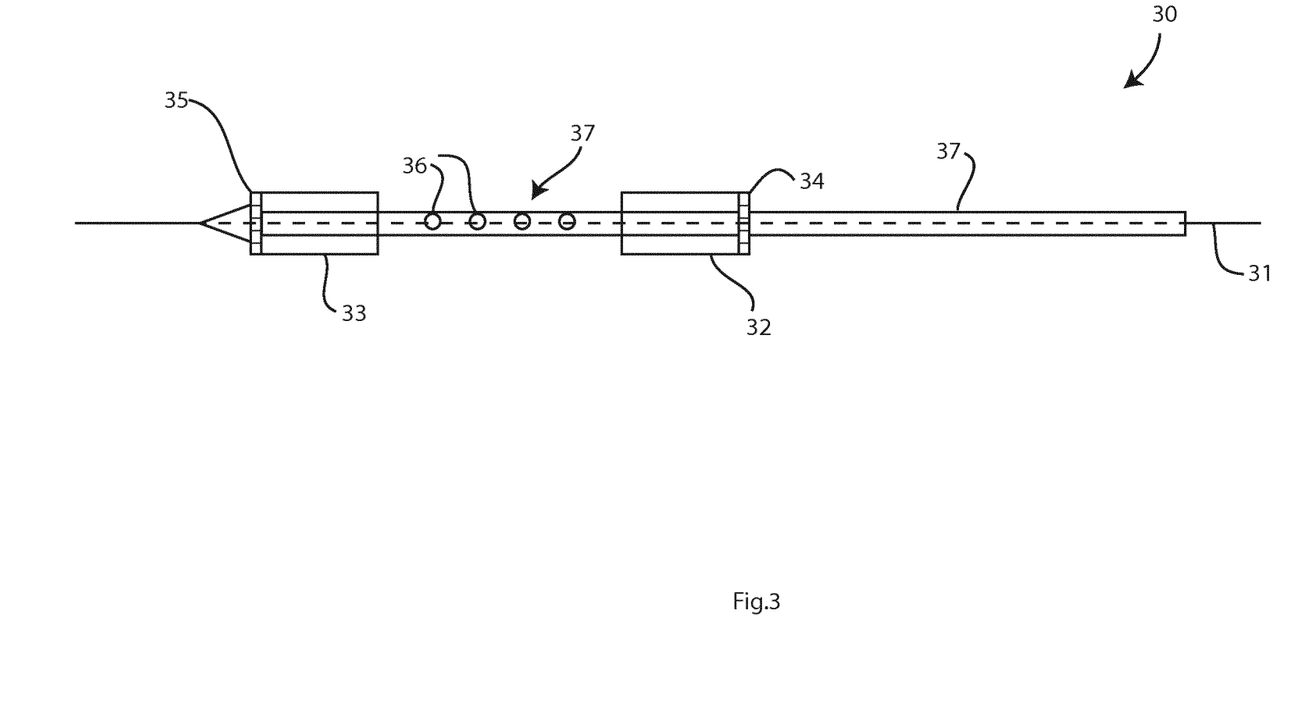
FIG. 3 is a diagram of the delivery system according to the invention.
Figure 4:
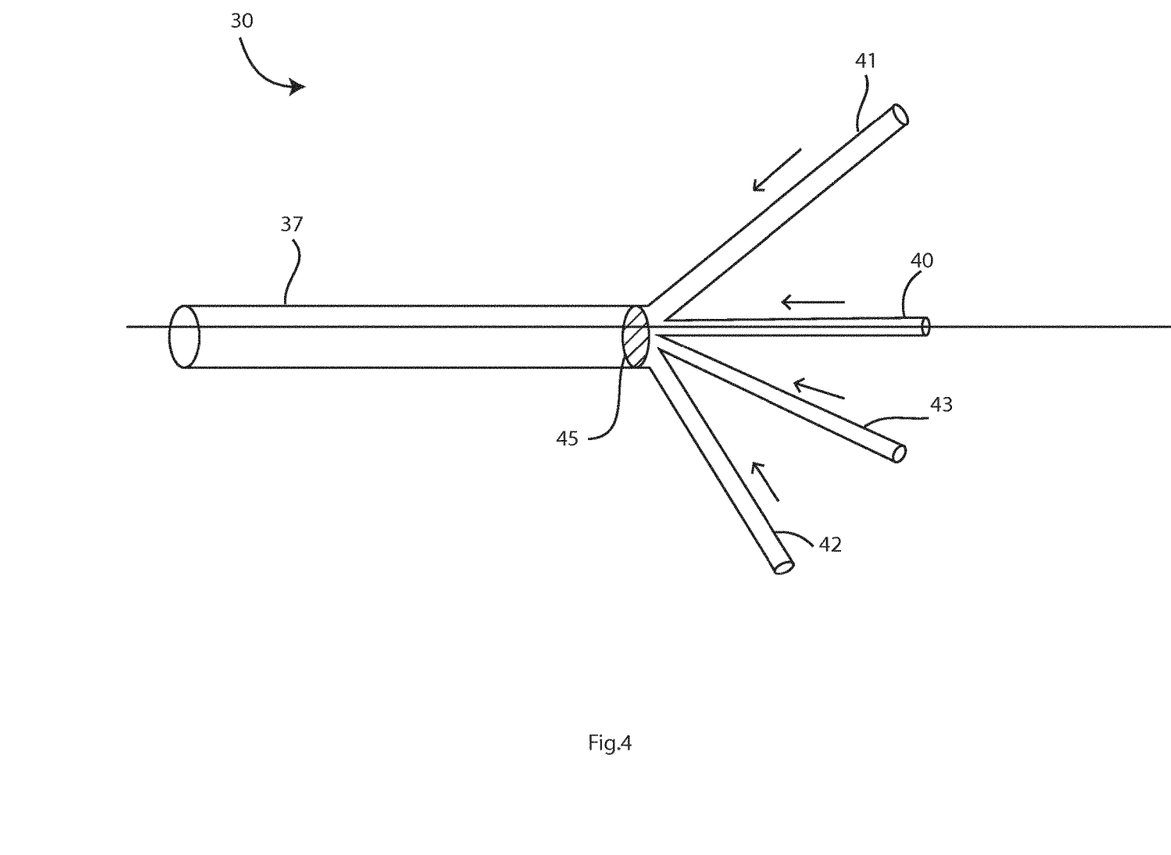
FIG. 4 is a more detailed diagram of the proximal end of the delivery system of FIG. 3.

The delivery system of the invention in one embodiment comprises a multi lumen catheter with typically four ports at the proximal end of the catheter to enable control of four functions at the distal end of the catheter that are used to deliver stem cell treatment. Some possible arrangements of the lumens are illustrated in FIGS. 3 and 4.

A first lumen is used for a guide wire with a pressure sensor. The guide wire may have a diameter suitable for the intended use. One such diameter is 0.014 mm guide wire. The catheter may be of a suitable size for use in the anterior tibial vena comitantes. For example the catheter may be 4 French or 5 French in size.

A second lumen is used for controlling the operation of a distal balloon which is located immediately proximal to the stem cell discharge device at the distal end. The purpose of the distal balloon is to occlude the vein and prevent the return of discharged stem cells. The balloon is inflated and deflated through one of the catheter lumens using saline mixed with radiopaque dye pumped into this balloon from the proximal end of the catheter.

A third lumen is used for control of the stem cell discharge device. The stem cell discharge device is located immediately proximal of the distal balloon. The operation of discharge chamber or stem cell discharge device is controlled from the proximal end of the catheter by at least one lumen. There are a number of ways in which the stem cell discharge device can discharge stem cells to the surrounding environment. The stem cells in suspension are ejected with sufficient force to overcome the pressure differential in the microcirculation system.

In one case stem cells are injected from the proximal handle of the catheter so that they travel through the lumen and into the discharge chamber and on into the micro circulation system.

Figure 5:
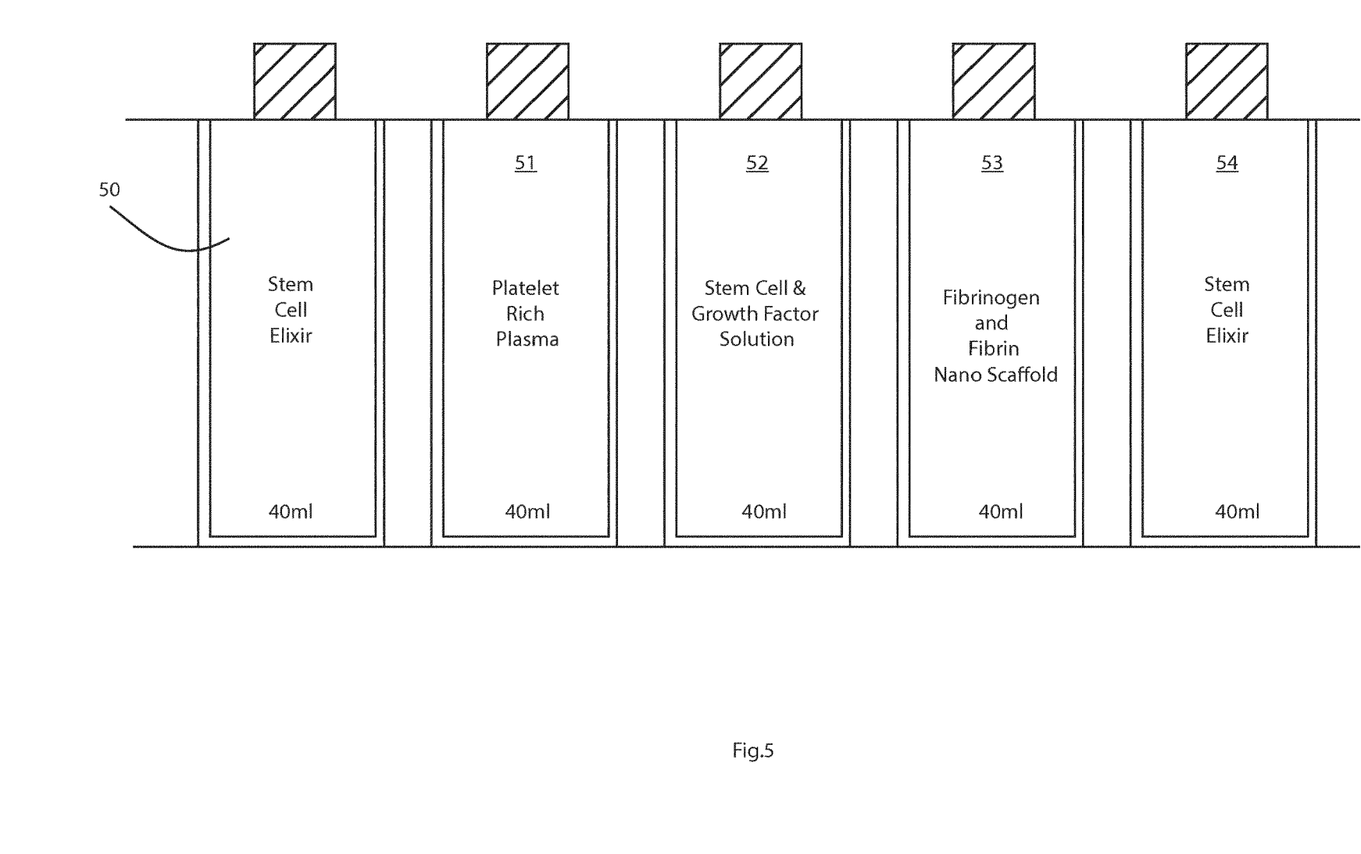
FIG. 5 is an illustration of different canisters for use with the delivery system.

The method of delivery occurs in five discreet stages. The first stage involves delivery of an elixir 50 which is delivered at a high pressure to open up the capillary bed. The pressure at which the elixir is injected is determined by the pressure reading on the sensor wire, such that the pressure at which the liquid is injected exceeds that of the wire reading, preferably up to a maximum of 90 mmHg, delivered over a time period of 10 to 20 mins, and preferably about 15 mins. The flow rate is preferably in the range of 1.0 to 1.4 ml/min.

The second infusion involves transmission of fluid containing the patient's own platelet-rich plasma, which has been harvested from the patient and centrifuged. This will be delivered at a pressure, which is again determined by the pressure reading on the guide wire. The pressure will be up to preferably 90 mmHg and the delivery will take place over 10 to 20 mins, preferably about 15 min. The flow rates are preferably in the range of 1.0 to 1.4 ml/min.

The third infusion will contain stem cells and growth factors and will take place at a low pressure of up to 25 mmHg and preferably between 20 to 25 mmHg, with flow rate of 0.33-0.44 ml/min. The duration is preferably in the range of 45 to 60 mins.

The fourth infusion will contain fibrin and fibronectin scaffolds and will be delivered slowly at an infusion rate of 0.33-0.44 ml/min, with delivery pressure not exceeding 25 mmHg.

The fifth and final infusion will once again contain elixir which will be infused slowly this time so as not to damage previously delivered products but rather to provide enrichment and nourishment for the stem cells. The infusion rate will range 0.33-0.44 ml/min, with delivery pressure not exceeding 25 mmHg.

A fourth lumen is used to control a smaller annular compliant balloon at the distal end of the catheter that is distal to the stem cell discharge device.

The proximal end of the catheter expands into connectors for the four or more lumen as described. The stem cell discharge process determines the nature of the hydraulic system control at the proximal end or handle. It may incorporate a simple fluid compression device similar in function to a syringe but with a more functionally adopted wider form factor. It may incorporate a motorized bidirectional pump such as used in high energy mechanical displacement functions. In this case two lumens may be assigned to hydraulics and the plunger at the distal end can be controlled to move forward and to be retracted.

Before removing the catheter assembly the balloons are deflated.

FIG. 3 is a view of the distal end of a delivery device 30 which has a catheter 37 through which there is a guide wire 31 such as a 0.014" pressure sensor guide wire. The catheter 37 preferably has a hydrophilic coating. There are proximal (3.5 mm) and distal (2.4 mm) balloons 32 and 33 with proximal and distal markers 34 and 35. There are four to six holes 36, in a spiral pattern to deliver stem cells, in-between the balloons 32 and 33. All holes are of equal diameter, measuring about 0.3 mm in diameter, arranged in a spiral pattern, equi-distance apart, over a length of 10 cm. In general there are preferably in the range of 2 to 10 holes, and more preferably 4 to 8 holes. The diameters are preferably 0.1 m to 0.5 mm, and most preferably about 0.2 mm to 0.4 mm.

FIG. 4 is a view of the proximal end of the catheter 37 with a delivery port 40 for the guide wire, a proximal balloon inflation port 41, a distal balloon inflation port 42, and a stem cell delivery port 43 which is connected to stem cell solution gun. The various lumens are connected via a one-way valve 45.

FIG. 5 is a view of five separate canisters which may be deployed in sequence during the treatment process. Each canister contains in one embodiment 40 ml of fluid. In order of delivery the contents of the canisters are: stem cell elixir 50, platelet rich plasma 51, stem cell and growth factor solution 52, (fibrinogen and fibrin) nanostructure scaffolds 53, and stem cell elixir 54.

Figure 6:
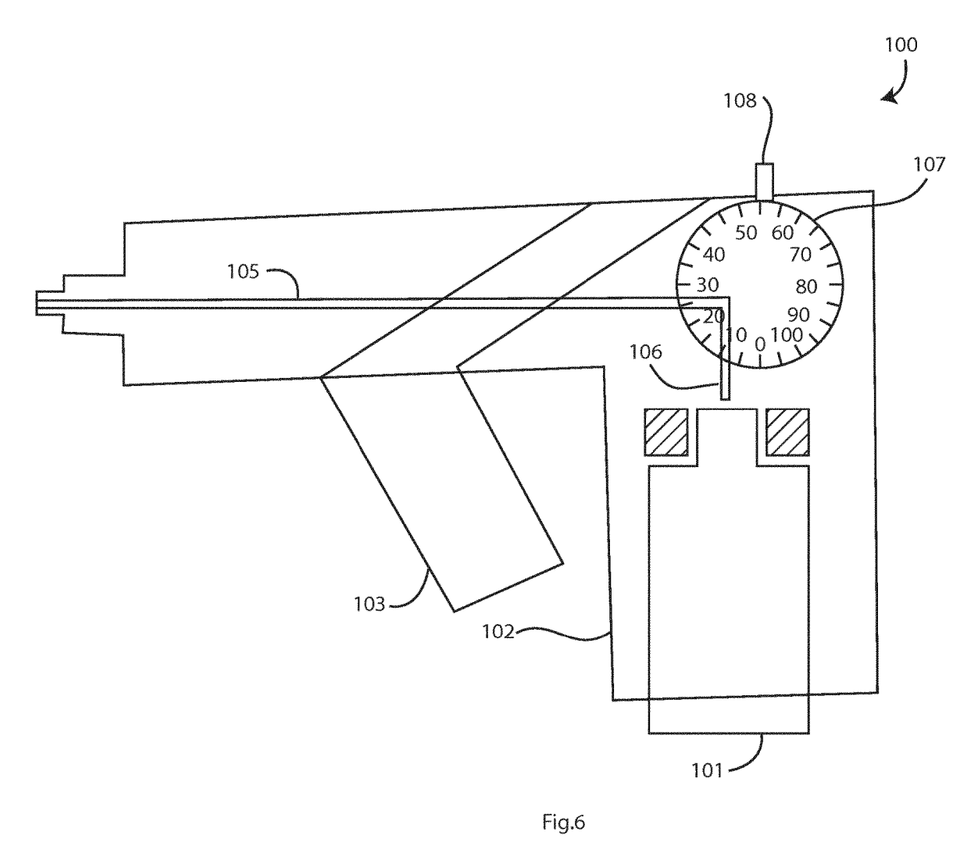
FIG. 6 is a diagram illustrating delivery from one canister.

FIG. 6 is a view of a stem cell solution gun 100. The canister 101 is loaded in turn into the vertical portion 102 of the gun, from below. The deployment pressure is determined according to the reading on the pressure guide wire. The deployment pressure is set using the pre-set button and the canister contents are deployed under pressure by firing of the gun trigger 103 The gun 100 has a high pressure tube 105 connected to a canister 101 by a one-way valve 106, and pressure is set to that which is appropriate for delivery by a monometer 107 having a pressure button 108.

The gun 6 is suitable for manual control of delivery, in terms of flow rates and pressure. However, in other embodiments an automated device has a processor and valves and timers for controlling these delivery parameters in a manner where human observation only is required rather than direct control. Also, it will be appreciated by those skilled in the art that any of a variety of mechanisms may be used to proximally control balloon inflation and delivery a series of agents to a delivery site. In one case the therapeutic agent may be stored locally in the discharge device between the balloons and released under mechanical or electronic control, and the latter may be wireless.

EXAMPLE

Cell delivery starts at low pressure 19-26 mmHg after high pressure 60-87 mmHg that opened the connection between veins and arteries, with infusion time over 120 minutes to protect the stem cell from apoptosis due to high pressure. The stem cell catheter and the gun both are thermally heated at 36° C. When we harvest the cells, they must be protected in an incubator at 36.5 to 37.5° C. to simulate the body temperature.

Figure 7:
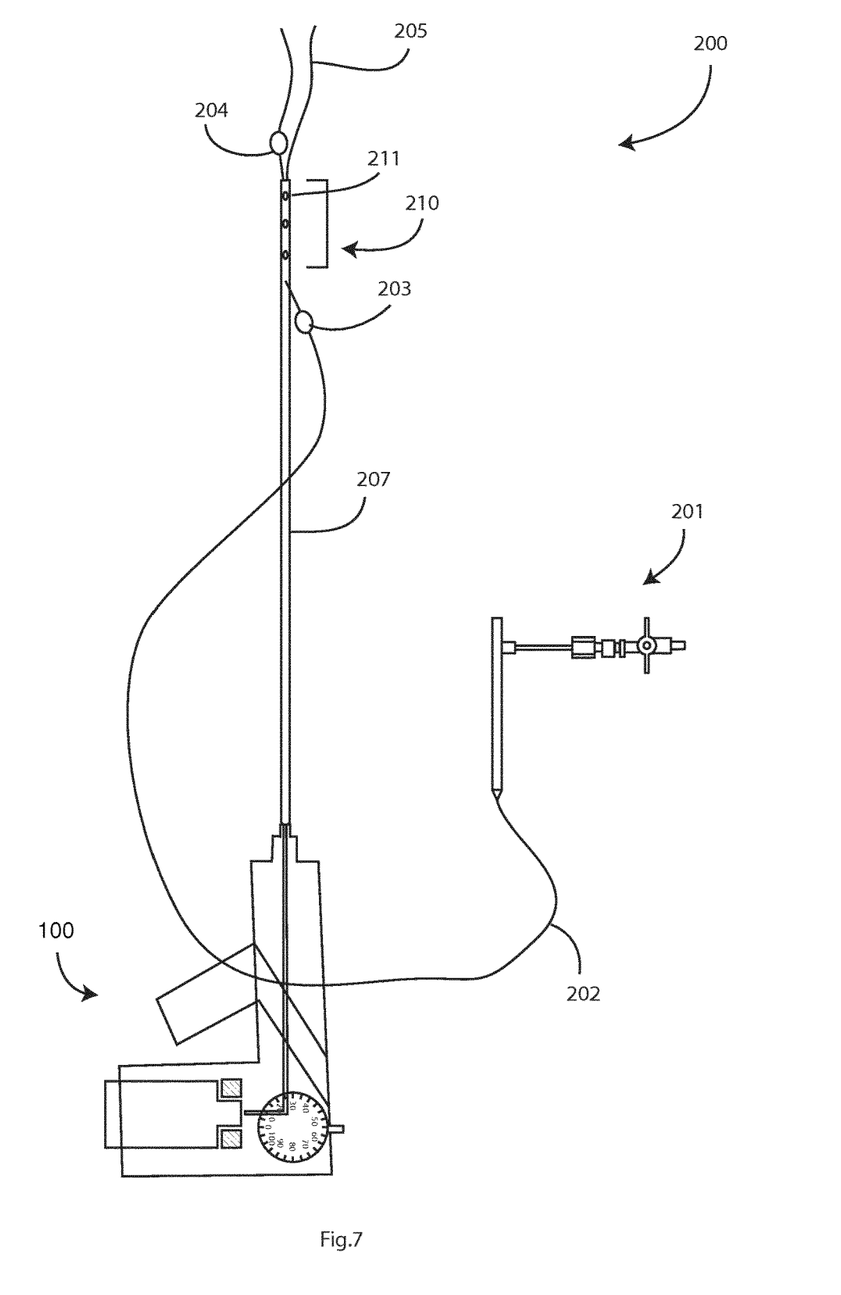
FIG. 7 is an illustration of a further delivery system.

Patient must be off any cytotxic drugs, statin, NSAID, DMRAD, antibiotics, Insulin, warfarin The wire sensor is used to monitor the pressure Test: Pressure Drop Measurements FIG. 7 shows a test apparatus 200 used to provide delivery measurements as set out below. The gun 100 is used for delivery of various agents such as those illustrated in FIG. 5. There is a flexible tube 202 for inflating a proximal balloon 203 and a distal balloon 204. The hand gun 100 delivers stem cells into a catheter 207 having a delivery site 210, with a number of holes 211. There is a sensor guide wire 205.

Pressure drop measurements along a 4 F catheter 207 to determine the optimum flow rate and delivery time for a "water like fluid" that will require an input pressure of less than 30 mmHg.

Method
Rig Setup:
Pressure Rig Components:
Guide wire 205,
4F Embolectomy catheter 207, 80 cm long, gun 100,
Harvard automatic pump,
pressure transducer, and
tubing and connectors 201, 202

The guide wire 205 was passed through the 4F catheter 207. A "T" junction allowed the connection of a pressure transducer and the gun 100 to the catheter 207. The gun 100 provided the flow rates presented in Table 1 below. Water was used as a test fluid. The far end of the catheter was left open. In this way the pressure at the distal end was considered 0 mmHg, while the pressure applied at the proximal end was recorded by the transducer.

Results

The delivery time and pressure values were recorded throughout the test. All measurements are presented in Table 1. It was found that for the 4F catheter, the flow rates below the threshold value of 0.57 ml/min produced internal fluid pressure of less than 30 mmHg.

TABLE 1

Pressure drop measurements

| Test number | Flow rate (ml/min) | Delivery time (min) | Pressure (mmHg) |
|---|---|---|---|
| 1 | 1.33 | 15 | 87 |
| 2 | 1.00 | 20 | 60 |
| 3 | 0.80 | 25 | 48 |
| 4 | 0.66 | 30 | 40 |
| 5 | 0.57 | 35 | 30 |
| 6 | 0.50 | 40 | 28 |
| 7 | 0.44 | 45 | 24 |
| 8 | 0.40 | 50 | 23 |
| 9 | 0.36 | 55 | 20 |
| 10 | 0.33 | 60 | 19 |

Most research to date utilizes Bone Marrow Mesenchymal Stem Cells BMMSC, for ethical reasons though other cells such as embryonic stem cells could perform equally well. However a cocktail of bone marrow, rich plasma concentrate and adipocyte derived stem cell may be used as such, in addition to allogenic stem cell delivery.

The stem cells may be delivered in any suitable medium such as medical grade saline or plasma derived from blood by centrifugal separation such as vascular endothelial growth factor VEGf.

Prior to the era of cellular therapy, gene therapy was proposed as a therapeutic option for CLI. Several phase 2 gene therapy clinical trials—with blood plasma components such as Vascular Endothelial Growth Factor (VEGF), Hypoxia-Inducible Factor 1a (HIF1a)/VP16, hepatocyte growth factor, and fibroblast growth factor 1 (FGF1)—have been completed and demonstrated their safety and feasibility in patients with Peripheral Arterial Disease/Peripheral Vascular Disease. The suspension media should sustain the stem cells while inhibiting adhesion to the storage or delivery media.

There is clinical evidence to show that stems cells can relieve blockage in arteries and promote angiogenesis. They can be partially differentiated or pre-programmed so that they adhere at a desired treatment location. ("Clinical application of vascular regenerative therapy for peripheral artery disease", Suzuki H, IsoY. Biomed Res Int. 2013; 2013: 179730. doi: 10.1155/2013/179730. Epub 2013 Nov. 24, and "The current state of stem cell therapy for peripheral artery disease" Gupta N K, Armstrong E J, Parikh S A. Curr Cardiol Rep. 2014 February; 16(2):447. doi: 10.1007/s11886-013-0447-2.)

Stem cells can be stored for both autologous and allogeneic use. The latter may be possible due to the immune-privileged status of these cells. This property offers substantial practical advantage in the clinical setting, especially when autologous cell transplantation would be ineffective because of disease-induced cell dysfunction. Furthermore, MSCs (BMMSCs) can be programmed to become a specific differentiated cell type prior to transplantation, thereby decreasing the likelihood of aberrant differentiation of MSCs after transplantation.

The therapeutic potential of mesenchymal stem cell transplantation in critical limbischemia is described by Liew and O'Brien in Stem Cell Research Therapy 2012, 3:28.

Stem cells are proven to be resistant to chemotherapy and to radiation and should tolerate high/elevated pressure for discharge.

Supramagnetic iron oxide nanoparticles targeting of MSCs in vascular injury is described by Reigler et al in Biomaterial 2012.11.040.

In the invention stem cells may have ultra-small paramagnetic Iron Oxide (USPIOs) particles (or similar nanoparticles) attached or placed in them to facilitate the use of a magnetic field or electromagnetic field to direct the motion and placement of the cells when they are they are delivered into a vein so that they cross the microcirculation system and enter an artery to a target site.

The invention is not limited to the embodiments hereinbefore described, with reference to the accompanying drawings, which may be varied in construction and detail. While the invention has been described with delivery into the venous system for delivery across a microcirculation system, it could also be considered as being directly into the microcirculation system due to the proximity of the delivery to the branch into the microcirculation system. This is best illustrated in FIG. 2. Also, the delivery could be in the venous system further from a branch into a microcirculation system, but at a location where the flow will cause the therapeutic agent to be conveyed across the microcirculation system.

What is claimed is:

1. A method for treatment of peripheral arterial occlusive disease, the method comprising steps of delivering a plurality of therapeutic agents into a venous system, across a microcirculation system and into an artery, said method comprising:
    a first infusion stage of delivering a stem cell elixir to open up a capillary bed with opening of collapsed venules in the microcirculation system, at a pressure up to a maximum of 90 mmHg,
    a second infusion stage of delivering an autologous or allogenic platelet-rich plasma, to prepare a vascular bed for the delivery of stem cells, at a pressure up to a maximum of 90 mmHg,
    a third infusion stage of delivering autologous or allogenic stem cells and growth factors, at a pressure up to 25 mmHg,
    a fourth infusion stage of delivering fibrin or fibronectin or fibrinogen nano-scaffolds, at a pressure up to a maximum of 25 mmHg, and
    a fifth infusion stage of delivering a stem cell elixir for enrichment of the stem cells.

2. The method as claimed in claim 1, wherein the infusion stages are performed while maintaining a thermo-balanced environment at a temperature of from 34° C. to 37° C. during all infusion stages.

3. The method as claimed in claim 1, wherein during said infusion stages pressure is monitored by a pressure wire sensor at a desired location of delivery.

4. The method as claimed in claim 1, wherein the plurality of therapeutic agents are delivered from a plurality of reservoirs.

5. The method as claimed in claim 1, wherein in said first infusion stage said stem cell elixir is delivered for a duration in the range of 10 min to 20 min.

6. The method as claimed in claim 1, wherein during said first infusion stage the stem cell elixir is delivered at a flow rate is in the range of 1.0 to 1.4 ml/min.

7. The method as claimed in claim 1, wherein said platelet-rich plasma of the second infusion stage has been harvested from the patient.

8. The method as claimed in claim 1, wherein during said second infusion stage said plasma is delivered at a flow rate in the range of 1.0 to 1.4 ml/min.

9. The method as claimed in claim 1, wherein in said third infusion stage said stem cells and growth factors are delivered at a flow rate of 0.33-0.44 ml/min over a period of 45 min to 60 min, so as not to damage the stem cells and their functional capacity.

10. The method as claimed in claim 1, wherein in said fourth infusion stage said nano-scaffolds are delivered at a flow rate in the range of 0.33 ml/min to 0.44 ml/min.

11. The method as claimed in claim 1, wherein during said fifth infusion stage the flow rate is in the range of 0.33 to 0.44 ml/min and the delivery pressure is from zero up to a maximum of 25 mmHg.

12. The method as claimed in claim 1, wherein the method is performed using a delivery system comprising a multi-lumen catheter for delivery of the therapeutic agents and a discharge device for location in a vein and being mounted to the catheter, wherein the system comprises a first balloon which is located proximally of the discharge device and a second balloon which is located distally of the discharge device, and a pressure stem cell solution delivery device configured to control said therapeutic agent delivery.

* * * * *